(12) United States Patent
Uchida et al.

(10) Patent No.: US 6,327,333 B1
(45) Date of Patent: Dec. 4, 2001

(54) TIRE INTERIOR INSPECTING METHOD AND TIRE INTERIOR INSPECTING SYSTEM FOR CARRYING OUT THE SAME

(75) Inventors: Norimichi Uchida; Takao Kokubu, both of Kodaira (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 09/517,692

(22) Filed: Mar. 2, 2000

(30) Foreign Application Priority Data

Mar. 3, 1999 (JP) .................................................. 11-056187

(51) Int. Cl.[7] .................................................. G01N 23/02
(52) U.S. Cl. .................................................. 378/61; 378/58
(58) Field of Search .................................. 378/57, 53, 62, 378/22, 61, 58

(56) References Cited

U.S. PATENT DOCUMENTS

| | | | |
|---|---|---|---|
| 4,350,942 | * 9/1982 | Heisner et al. | 318/626 |
| 4,928,297 | * 5/1990 | Tsutsui et al. | 378/146 |
| 4,949,366 | * 8/1990 | Collmann | 378/61 |
| 5,583,904 | * 12/1996 | Adams | 378/17 |
| 6,023,497 | * 2/2000 | Takahashi et al. | 378/57 |

* cited by examiner

Primary Examiner—Robert H. Kim
Assistant Examiner—Irakli Kiknadze
(74) Attorney, Agent, or Firm—Sughrue Mion, PLLC

(57) ABSTRACT

A tire interior inspecting method irradiates a tire being continuously conveyed by a conveyor with x-rays emitted from a predetermined position, receives the x-rays penetrated through the tire by a high resolution linear x-ray sensor to obtain x-ray information about the tire, compares the x-ray information with normal tire image information about the metallic components of a normal tire, removes parts of the x-ray image information coinciding with the normal tire image information, and decides the quality of interior of the tire on the basis of image information obtained by removing parts of the x-ray image information coinciding with the normal timer image information.

8 Claims, 7 Drawing Sheets

F I G. 5
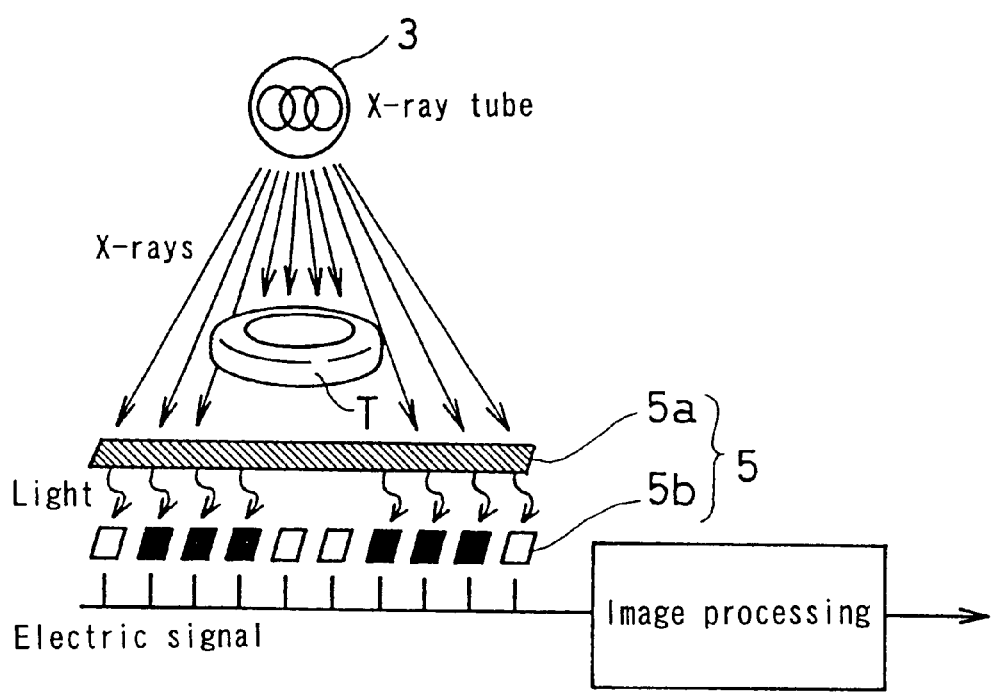

FIG. 7A
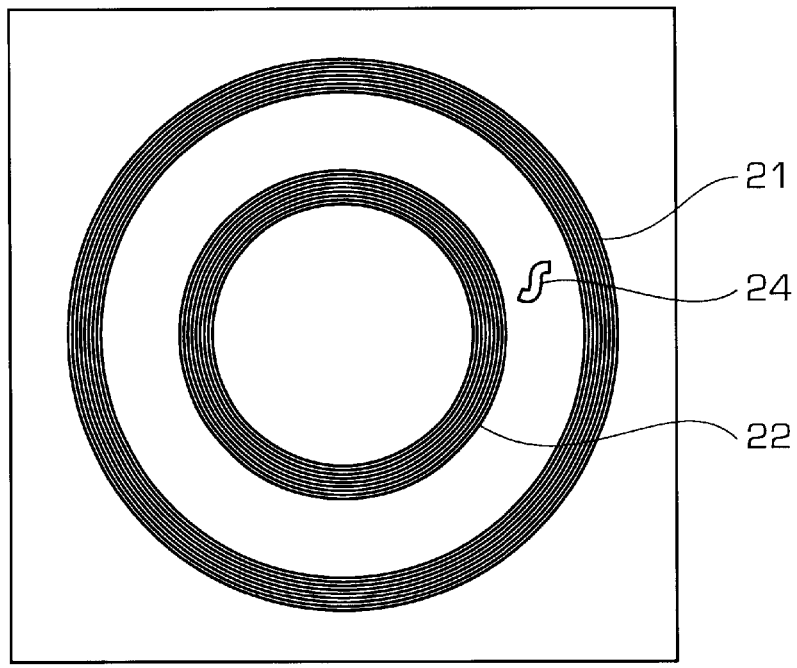
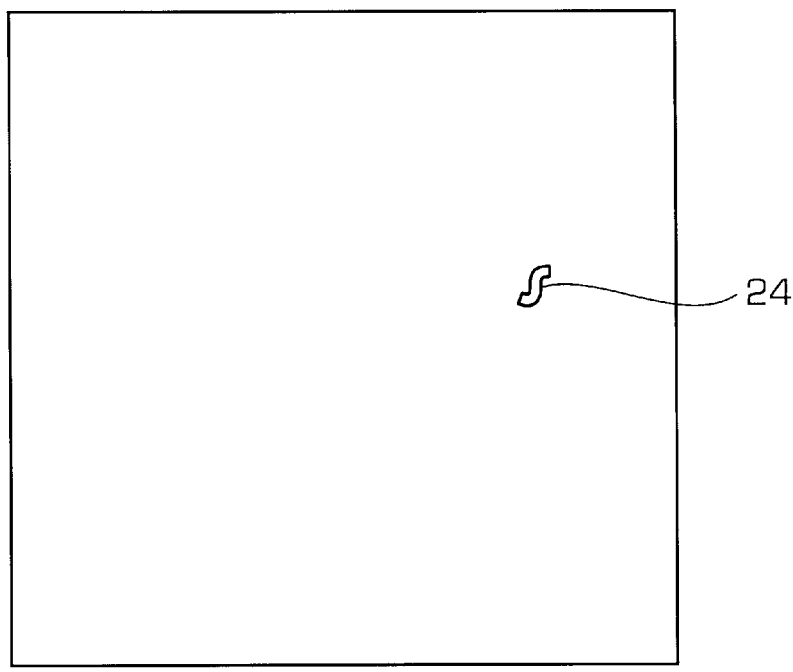
FIG. 7B

TIRE INTERIOR INSPECTING METHOD AND TIRE INTERIOR INSPECTING SYSTEM FOR CARRYING OUT THE SAME

BACKGROUND OF THE INVENTION

1. Field of the Invention

The present invention relates to a tire interior inspecting method and a tire interior inspecting system using x-rays for inspecting the interior of a tire.

2. Description of the Related Art

When inspecting tires, a sample tire is taken from a tire manufacturing line, the sample tire is set on an x-ray photographing apparatus to form an x-ray image of the interior of the sample tire by using an x-ray film or an image intensifier, and the x-ray image of the interior of the sample tire is examined visually by the operator. A tire conveying line must be stopped every time a tire is sampled, which reduces the productivity of the tire manufacturing line. Therefore, the total inspection of tires is practically impossible and, consequently, tires must be inspected by sampling inspection. A final decision about the quality of the interior of the tire must be made by the operator on the basis of the results of visual inspection of the x-ray image. Decisions based on the results of visual inspection include subjective errors, and the operator's subjective decision is unsuitable for determining rigorous numerical quality assurance references. It is difficult to exclude differences in decision between the operators.

A tire conveyor of the tire conveying line is operated at a very high conveying speed to let a tire pass a fixed position in about 2s. Therefore, the total inspection of tires by the operator is impossible. A special high-speed image processing system is expensive and the development of the special high-speed image processing system involves economical risk.

SUMMARY OF THE INVENTION

Accordingly, it is an object of the present invention to provide a tire interior inspecting method and an inexpensive tire interior inspecting system capable of automatically inspecting tires being conveyed by a tire conveyor for total inspection without stopping the tire conveying line.

According to a first aspect of the present invention, a tire interior inspecting method comprises the steps of: irradiating a tire being continuously conveyed by a conveyor with x-rays emitted from a predetermined position; receiving the x-rays penetrated through the tire by a high-resolution linear x-ray sensor to obtain x-ray image information about the tire; comparing the x-ray image information with normal tire image information about the metallic components of a normal tire; and deciding the quality of the interior of the tire.

An x-ray image of the tire being continuously conveyed by the tire conveyor can be formed by the high-resolution liner x-ray sensor, and the quality of the interior of the tire is decided on the basis of the result of comparison of the x-ray image information and the normal tire image information, and hence a quality deciding process can be quickly achieved.

Thus, all the tires being conveyed by the tire conveyor can be inspected for total inspection without stopping the tire conveying line.

In this tire interior inspecting method, the step of comparing the x-ray image information with the normal tire image information carries out an image processing process that uses an image of one or a plurality of annular parts corresponding to the component members of the normal tire as normal tire image information representing the normal tire and removes parts of the x-ray image information about the tire coinciding with the normal tire image information representing the normal tire, and the step of deciding the quality of interior of the tire decides the quality of the interior of the tire on the basis of an image obtained by thus processing the x-ray image information by the image processing process.

The image processing process that removes the parts of the x-ray image information coinciding with the normal tire image information representing one or a plurality of annular images of the component members of the normal tire makes images of irregularly arranged wires and foreign matters stand in strong relief, which facilitates quick decision of the quality of the interior of the tire.

In the step of comparing the x-ray image information with the normal tire image information in this tire interior inspecting method, the normal tire image information may be superposed on the x-ray image information to obtain superposed image information, and parts of the x-ray image information about the tire coinciding with the normal tire image information may be removed by the image processing process, and the quality of the interior of the tire may be decided on the basis of an image obtained by thus processing the x-ray image information by the image processing process.

According to a second aspect of the present invention, a tire interior inspecting system comprises: an x-ray irradiating means for irradiating a tire being continuously conveyed by a conveyor with x-rays from a predetermined position; a high-resolution linear x-ray sensor capable receiving x-rays penetrated the tire to obtain x-ray image information; a comparing means for comparing the x-ray image information with normal tire image information about metallic components of a normal tire; and a quality deciding means for deciding quality of interior of the tire on the basis of result of comparison of the x-ray image information with the normal tire image information.

The high-resolution linear x-ray sensor is capable of obtaining x-ray image information about the tire while the tire is being continuously conveyed by the conveyor, the comparing means compares the x-ray image information with the normal tire image information about the metallic components of the normal tire, and the quality deciding means decides the quality of the interior of the tire on the basis of the result of comparison of the x-ray image information with the normal tire image information.

Thus, a quality deciding process for deciding the quality of the interior of the tire can be quickly achieved. Thus, all the tires can be automatically inspected for total inspection without stopping the tire conveying line.

In this tire interior inspecting system, the comparing means may be an image processing means that superposes the normal tire image information on the x-ray image information to obtain superposed image information, and removes parts of the x-ray image information coinciding with the normal tire image information by the image processing process, and the quality deciding means may decide the quality of the interior of the tire on the basis of an image obtained by thus processing the x-ray image information by the image processing means.

Since the image processing means superposes the normal tire image information on the x-ray image information to obtain the superposed image information and removes parts of the x-ray image information coinciding with the normal tire image information, and the quality deciding means decides the quality of the interior of the tire on the basis of an image obtained by thus processing the x-ray image information by the image processing means, the quality of the interior of the tire can be quickly decided without requiring any special high-speed image processing apparatus.

In this tire interior inspecting system, the high-resolution linear x-ray sensor may have a resolution not greater than the diameter of the tire cords of the tire.

When the high-resolution linear x-ray sensor has a resolution not greater than the diameter of the tire cords, irregular wires, such as belt wires, i.e., components of the tire, and foreign matters including small metal pieces and small stones can be easily detected.

BRIEF DESCRIPTION OF THE DRAWINGS

The above and other objects, features and advantages of the present invention will become more apparent from the following description taken in connection with the accompanying drawings, in which:

FIG. 5 is a pictorial view of assistance in explaining the principle of forming an x-ray image by the tire interior inspecting system shown in FIG. 1;

FIGS. 7A and 7B are a view showing an x-ray image of a tire and a view of an image obtained by processing the x-ray image.

DESCRIPTION OF THE PREFERRED EMBODIMENTS

Figure 1:
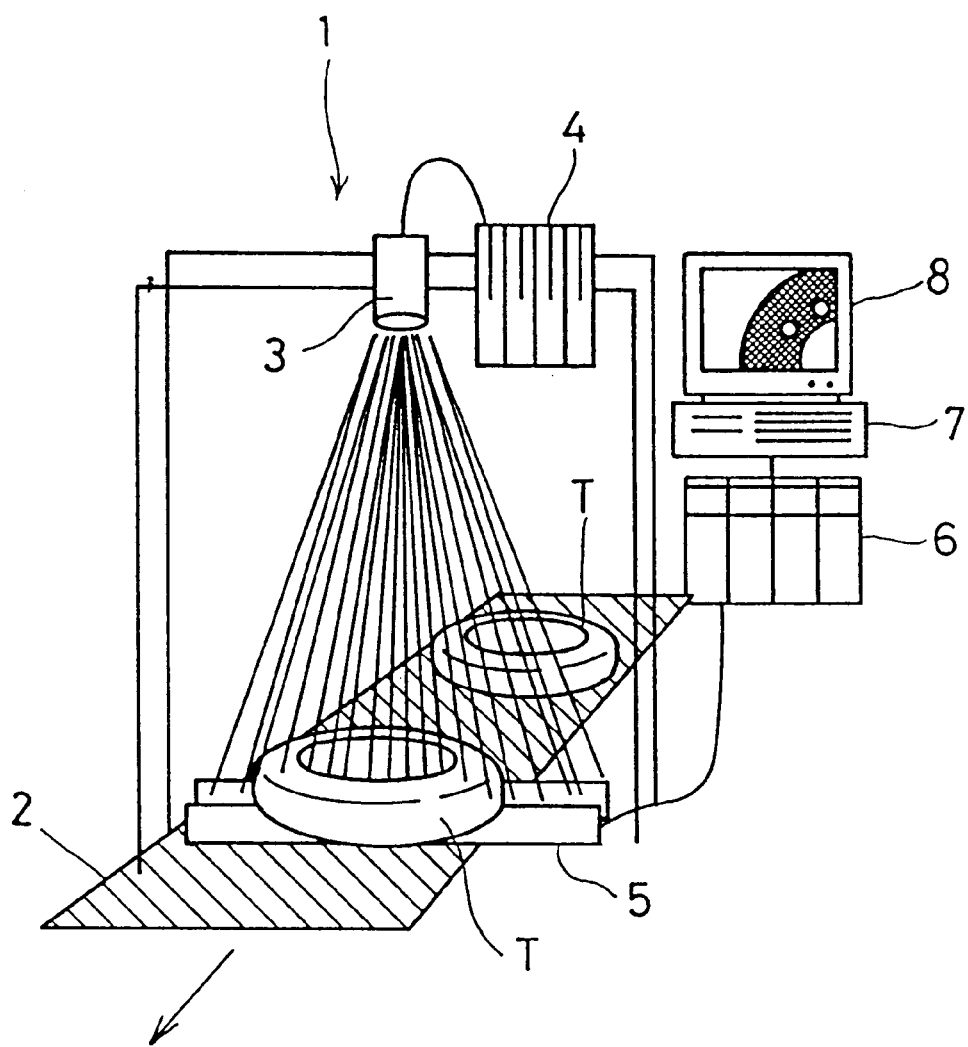
FIG. 1 is a schematic perspective view of a tire interior inspecting system in a preferred embodiment according to the present invention.

Referring to FIG. 1 showing a tire interior inspecting system 1 in a preferred embodiment according to the present invention, vulcanized tires T are conveyed successively by a continuously operating roller conveyor 2. An x-ray tube 3, i.e., an x-ray source, is disposed at a predetermined position above the roller conveyor 2 to irradiate x-rays downward. The x-ray tube is driven by an x-ray generator 4. A linear x-ray sensor 5 is disposed directly below the x-ray tube 3 at a position corresponding to a space between two adjacent conveyor rollers 2a (FIG. 2) to detect x-rays irradiated by the x-ray tube 3. Thus a curtain of x-rays perpendicular to a direction in which the tires T are conveyed is formed between the x-ray tube 3 and the linear x-ray sensor 5. Consequently, the tires T are conveyed across the curtain of x-rays. The linear x-ray sensor 5 detects x-rays penetrated the tire T moving across the curtain of x-rays and fallen thereon, and provides a detection signal. An image processor 6 receives the detection signal provided by the linear x-ray sensor 5, and processes the detection signal to form an x-ray image of the tire T. A computer 7 decides the quality of the interior of the tire T on the basis of the image formed by the image processor 6. The image formed by processing the detection signal is displayed on the screen of a monitor 8.

Figure 2:
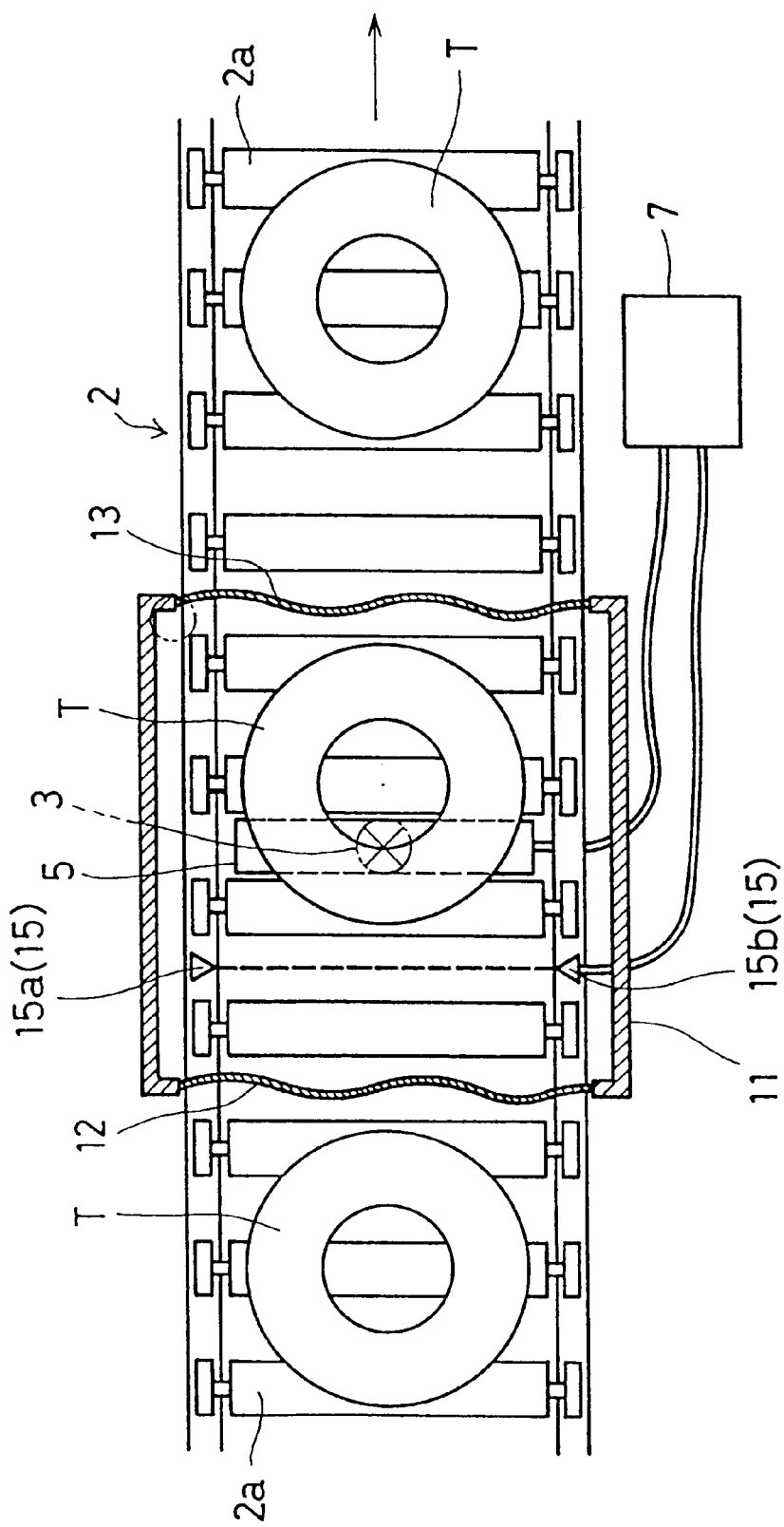
FIG. 2 is a plan view of assistance in explaining an x-ray irradiating operation of the tire interior inspecting system shown in FIG. 1.
Figure 3:
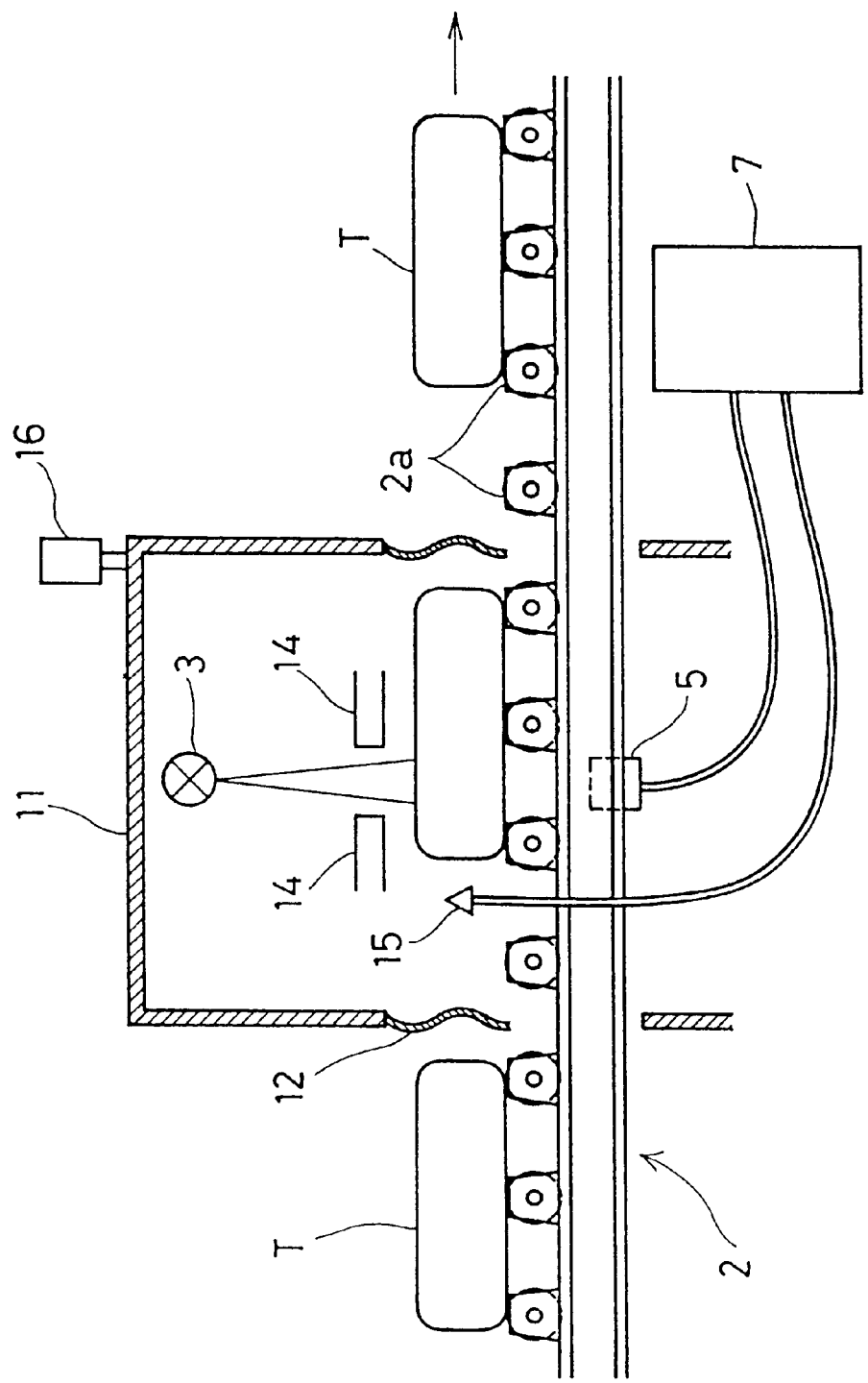
FIG. 3 is a partly sectional schematic side elevation of the tire interior inspecting system shown in FIG. 1.
Figure 4:
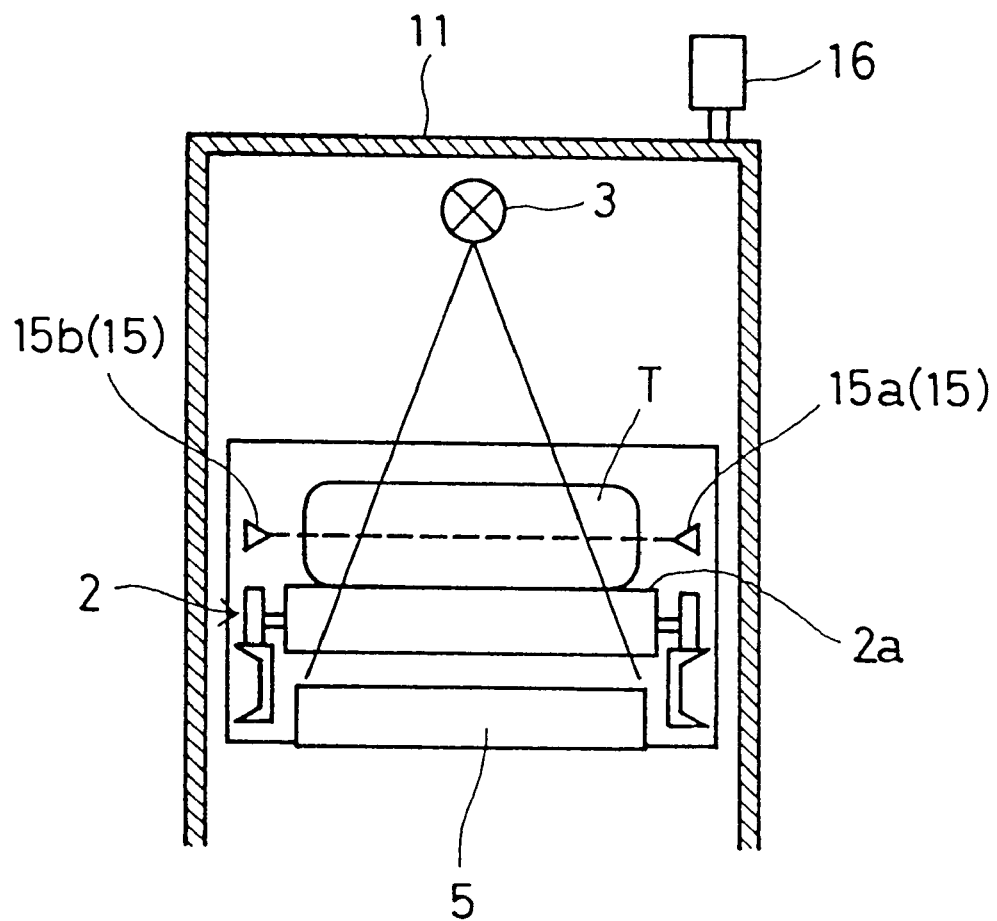
FIG. 4 is a front elevation of the tire interior inspecting system shown in FIG. 1.

FIGS. 2 to 4 show an x-ray irradiating structure of the tire interior inspecting system 1. The roller conveyor 2 is formed by arranging the plurality of conveyor rollers 2a driven for rotation. A predetermined section of the roller conveyor 2 is covered with a shielding lead box 11. An entrance opening through which the tires T enter the shielding box 11 and an exit opening through which the tires T leave the shielding box 11 are only openings in the shielding box 11. The entrance and the exit opening are covered with lead curtains 12 and 13, respectively.

The x-ray tube 3 is disposed in an upper region of a space defined by the shielding box 11, and the linear x-ray sensor 5 is disposed under a space between the adjacent conveyor rollers 2a. A slit plate 14 provided with a slit is disposed between the x-ray tube 3 and the roller conveyor 2 to define a passage for x-rays traveling from the x-ray tube 3 toward the linear x-ray sensor 5. The height of the slit plate 14 is determined so that the slit plate may not interfere with the tires T being conveyed by the roller conveyor 2. Thus, x-rays emitted by the x-ray tube 3 travels through the slit of the slit plate 14 toward the linear x-ray sensor 5 in a curtain of x-rays crossing a conveying path along which the tires T are conveyed.

A photoelectric switch 15 including a light emitting device 15a and a light receiving device 15b is disposed on the entrance side of the curtain of x-rays to detect the tire T moved through the entrance opening into the shielding lead box 11 upon the arrival of the tire T at a position immediately in front of the curtain of x-rays. An x-ray photographing operation is timed by the photoelectric switch 15. Upon the detection of the tire T by the photoelectric switch 15, the x-ray photographing operation is started. Upon the detection of the tire T, the photoelectric switch 15 sends a detection signal to the computer 7, and then the computer 7 controls the x-ray tube 3 for x-ray irradiation. A pilot lamp 16 disposed on top of the top wall of the shielding lead box 11 is turned on while the x-ray lamp 3 is turned on to emit x-rays.

The principle of the principle of forming an x-ray image by the tire interior inspecting system 1 will be described with reference to FIG. 5. The linear x-ray sensor 5 has a linear scintillator 5a that emits light when irradiated with x-rays, and photodiodes 5b, i.e., photoelectric devices, arranged opposite to the scintillator 5a. The linear x-ray sensor 5 is suitable particularly for x-ray photographing a moving object. The liner x-ray sensor 5 has a high resolution of 0.4 mm/pixel, which is smaller than the diameter of about 1 mm of wires, i.e., components of the tire, forming a part of a belt corresponding to the crown of the tire.

Figure 6A:
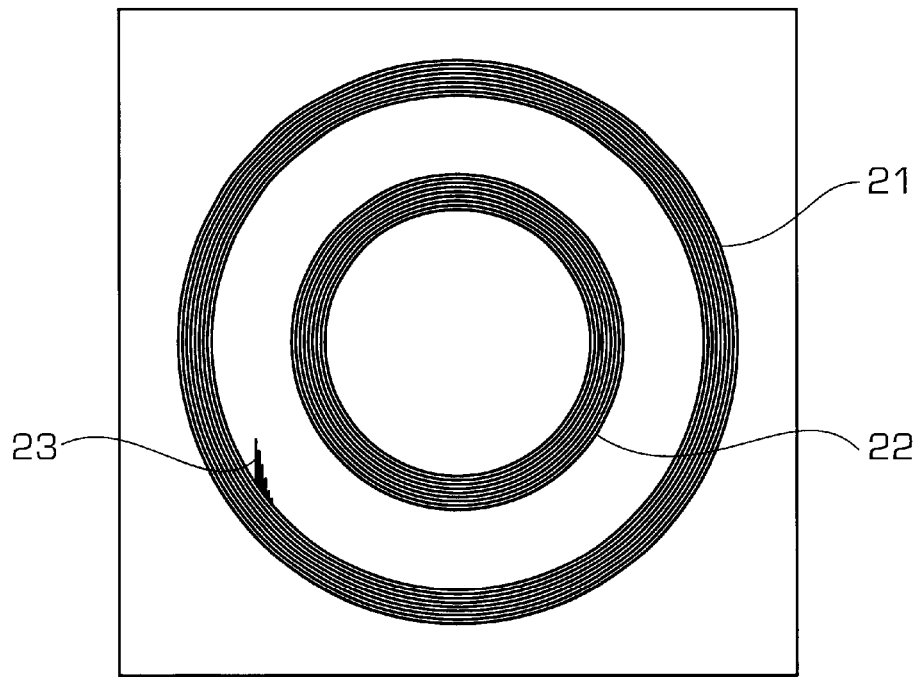
FIGS. 6A and 6B are a view showing an x-ray image of a tire and a view of an image obtained by processing the x-ray image, respectively.
Figure 6A:
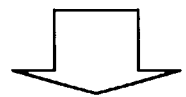

X-rays emitted by the x-ray tube 3 in a curtain and traveled through the tire T are detected by the linear x-ray sensor 5. Then, the linear x-ray sensor 5 gives an electric signal corresponding to the x-rays fallen thereon to the image processor 6. Then, the image processor 6 processes the electric signal to form an x-ray image. The x-ray image clearly shows belt wires and bead wires, i.e., the metal components of the tire T, in a high resolution of 0.4 mm/pixel. As shown in FIGS. 6A (FIG. 7A), an outer circular image 21 of a great diameter is an image of belt wires in the crown of the tire T, and an inner circular ring 22 of a small diameter is an image of bead wires in the bead of the tire T.

Figure 6B:
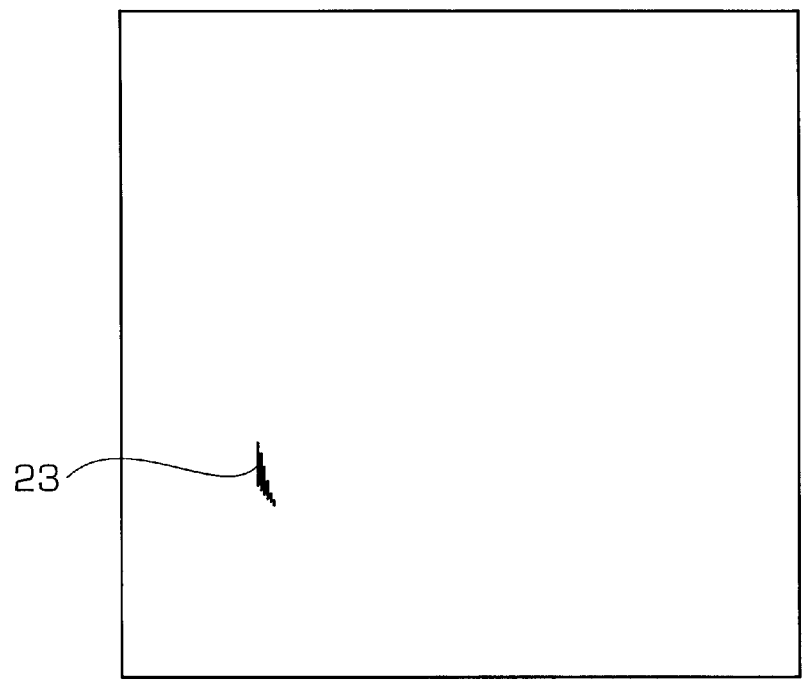

If the tire T has irregularly arranged wires, an image 23 of the irregularly arranged wires is formed as shown in FIG. 6A. A foreign matter, such as a small metal piece or a small stone, an image 24 of the foreign matter is formed as shown in FIG. 7A. A normal x-ray image of a normal tire is stored beforehand in the image processor 6. The image processor 6 superposes the normal x-ray image on the x-ray image of the tire T and removes a part of the x-ray image of the tire T coinciding with the normal x-ray image to obtain an image shown in FIG. 6B (FIG. 7B). When parts of the x-ray image of the tire T having irregularly arranged parts of the belt wires shown in FIG. 6A coinciding with the normal x-ray image are removed, the image 23 of the irregularly arranged parts of the belt wires can be clearly shown as shown in FIG. 6B. When parts of the x-ray image of the tire T containing a foreign matter shown in FIG. 7A coinciding with the normal x-ray image are removed, the image 24 of the foreign matter can be clearly shown as shown in FIG. 7B. The computer 7 is able to recognize the image we of the irregularly arranged parts of the belt wires or the image 24 of the foreign matter quickly with reliability. Thus, a decision as to whether or not the internal quality of the tire is acceptable can be very quickly made. The images 23 and 24 can be represented numerical values to decide the interior quality of the tire according to criteria.

The conveying speed of the roller conveyor 2 is 40 m/min. The tires T are arranged on the roller conveyor 2 so that the tires T pass the curtain of x-rays at intervals of about 2s. Thus, the tire interior inspecting system 1 carries out a tire interior inspecting cycle including the steps of x-ray photographing, image processing and quality deciding every 2s for each tire T. Such quick interior quality decision can be achieved because the high-resolution linear x-ray sensor 5 employing the scintillator 5a is capable of taking an x-ray photograph of the moving tire T, the image processor 6 is capable of superposing the previously stored normal x-ray image of the normal tire with the x-ray image of the tire T and of removing parts of the x-ray image coinciding with the normal x-ray image to show clearly only the image of the irregularly arranged parts of the wires or the foreign matter contained in the tire T for the quick decision of the quality of the interior of the tire T.

Thus, the all the tires T can be successively and automatically inspected without stopping the roller conveyor 2 of the tire conveying line. Since the tires T can be automatically inspected, the inspection does not need any inspector, the subjective decision of the inspector can be avoided, the quality of the tires can be decided according to the numerical criteria and hence the level of quality assurance can be raised.

The resolution of the linear x-ray sensor 5 need not be 0.4 mm/pixel and may be any suitable value. When the linear x-ray sensor 5 has a resolution smaller than the diameters of the component wires of the tire, irregularly arranged parts of the wires and foreign matters of sizes greater than the resolution can be detected.

Although the image processor 6 carries out the image processing process for superposing the previously stored normal x-ray image of the normal tire on the x-ray image of the tire T and removing parts of the x-ray image of the tire T coinciding with the normal x-ray image, the image processor 6 may carry out an image processing process that uses one or a plurality of annular images corresponding to the components of the tire and removes parts of the x-ray image of the tire T corresponding to the one or the plurality of annular images.

Although the present invention has been described as applied to the inspection of vulcanized tires, naturally, the present invention is applicable to the inspection of green tires before vulcanization.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A tire interior inspecting method comprising the steps of:

conveying a tire on a roller conveyor having spaced-apart parallel conveyor rollers;

irradiating x-rays from an X-ray irradiating unit at a predetermined position on to and through the tire being conveyed on said roller conveyor within an x-ray curtain extending in a longitudinal direction of the conveyor rollers, and causing the x-ray curtain to pass through a gap between adjacent conveyor rollers;

detecting the x-rays, that have passed through the tire being conveyed on the roller conveyor, by a high-resolution linear x-ray sensor, and obtaining x-ray image information of the tire;

providing a normal tire image information including at least one metallic ring component constituting a normal tire;

removing said normal tire image information from said x-ray image information to obtain a residual image; and determining whether there is a defective interior quality of the tire when said residual image includes an irregularity.

2. The tire interior inspecting method according to claim 1, wherein said removing step is performed by superposing said normal tire image information with said x-ray image information.

3. The tire interior inspecting method according to claim 1, wherein said step of determining is based on the presence of foreign matter in said residual image.

4. A tire interior inspecting system comprising;

a roller conveyor including spaced-apart parallel conveyor rollers on which a tire is conveyed;

an x-ray irradiating unit provided at a predetermined position with respect to said roller conveyor to irradiate x-rays on to and through the tire being conveyed on said roller conveyor within an x-ray curtain extending in a longitudinal direction of the conveyor rollers, said x-ray curtain passing through a gap between adjacent conveyor rollers;

a high-resolution linear x-ray sensor that detects the x-rays that have passed through the tire being conveyed on the roller conveyor and obtains x-ray image information about the tire;

image comparing and processing means for comparing normal tire image information including at least one metallic ring component constituting a normal tire with said x-ray image information and for removing said normal tire image information from said x-ray image information to obtain a residual image; and determining means for determining whether there is defective interior quality of the tire when the residual image includes an irregularity.

5. The tire interior inspecting system according to claim 4, wherein said image comparing and processing means includes an image processing means that performs an image processing operation for superposing said normal tire image information with said x-ray image information to remove the normal tire image information from the x-ray image information.

6. The tire interior inspecting system according to claim 4, wherein said high-resolution linear x-ray sensor has a resolution smaller than diameters of said metallic ring components.

7. The tire interior inspecting system according to claim 4, wherein said determining means determines a defect based on the presence of foreign matter.

8. The tire interior inspecting system according to claim 4, wherein said at least one metallic ring component is a belt ply or a bead.

* * * * *